US006313356B1

(12) United States Patent
Kohler et al.

(10) Patent No.: US 6,313,356 B1
(45) Date of Patent: Nov. 6, 2001

(54) PROCESS FOR THE PREPARATION OF CYCLOOCTANOL

(75) Inventors: Guenther Kohler; Manfred Kaufhold, both of Marl; Renate Paulczynski, Herne; Michael Beuth, Dorsten, all of (DE)

(73) Assignee: Degussa Huels AG, Frankfurt (DE)

( * ) Notice: Subject to any disclaimer, the term of this patent is extended or adjusted under 35 U.S.C. 154(b) by 0 days.

(21) Appl. No.: 09/663,928

(22) Filed: Sep. 18, 2000

(30) Foreign Application Priority Data

Sep. 18, 1999 (DE) .............................................. 199 44 874

(51) Int. Cl.[7] .................................................... C07C 35/20
(52) U.S. Cl. ................................................................ 568/821
(58) Field of Search .............................................. 568/821

(56) References Cited

U.S. PATENT DOCUMENTS

| 3,609,182 | * | 9/1971 | Baker | .................................... | 568/821 |
| 4,506,105 | * | 3/1985 | Kaufhold | .............................. | 568/821 |
| 5,475,158 | * | 12/1995 | Krug | .................................... | 568/821 |
| 6,093,857 | | 7/2000 | Fischer et al. | . | |

FOREIGN PATENT DOCUMENTS 1 153 468   5/1969   (GB) .

\* cited by examiner

*Primary Examiner*—Michael L. Shippen
(74) *Attorney, Agent, or Firm*—Oblon, Spivak, McClelland, Maier & Neustadt, P.C.

(57) ABSTRACT

A process for the preparation of cyclooctanol from cyclooctene comprising:
  a. reaction of cyclooctene with formic acid in the absence of an added catalyst to produce a two-phase reaction mixture containing cyclooctyl formate and residual formic acid,
  b. separation of the two phases into a lower phase rich in formic acid (phase A) and an upper phase low in formic acid (phase B),
  c. extraction of cyclooctyl formate from phase A to obtain an extract,
  d. combination of phase B and the extract from phase A,
  e. distillative work-up of the combination of phase B and the extract from phase A in an apparatus fitted with a short distillation path to obtain crude cyclooctyl formate, and
  f. catalytic transesterification of the cyclooctyl formate of said crude cyclooctyl formate with an alcohol to produce cyclooctanol.

20 Claims, No Drawings

PROCESS FOR THE PREPARATION OF CYCLOOCTANOL

BACKGROUND OF THE INVENTION

1. Field of the Invention

The invention relates to a process for the preparation of cyclooctanol by reaction of cyclooctene with formic acid to give cyclooctyl formate, phase separation after the reaction into a lower A phase rich in formic acid (formic acid content >60%) and an upper B phase low in formic acid (formic acid content <20%), extraction of cyclooctyl formate from the A phase, combination of this extract with the B phase, gentle distillative work-up of the reaction mixture which contains the cyclooctyl formate via a short distillation path, and transesterification of the cyclooctyl formate to give cyclooctanol.

2. Discussion of the Background

Cyclooctanol is an important intermediate for the preparation of, inter alia, cyclooctanone, which is required in the pharmaceutical sector, and for the preparation of fragrances. Syntheses of cyclooctanol from cyclooctene via the formate are known from the literature. For example, GB 1 153 468 describes a process in which formic acid is added to cyclooctene without catalyst, the reaction mixture is worked up distillatively and the cyclooctyl formate thus obtained is hydrolyzed with sodium hydroxide solution. It is pointed out that the temperatures during the distillation must be very low. In order to avoid decompositions, temperatures of less than 100° C. are required. However, in the case of industrial implementation, this requirement cannot be realized and, even in Example 1, a temperature above 100° C. is given as the boiling point of the formate. The relatively poor yield of only 82% based on reacted cyclooctene is attributable to thermal decomposition. A further disadvantage of this process is that the hydrolysis of the formate using sodium hydroxide solution produces at least stoichiometric amounts of sodium formate, which have to be disposed of.

The object of the invention was therefore to find a process which is easy to carry out industrially and in which such thermal decomposition does not take place and in which no noteworthy amounts of salts are produced as waste material.

SUMMARY OF THE INVENTION

The object is achieved according to the invention by carrying out the reaction of cyclooctene with formic acid in the absence of an added catalyst, carrying out the distillation continuously without a column over a short path and transesterifying the resulting ester with an alcohol.

Surprisingly, it has, in particular, been found that the distillation can be carried out without great separation effort in an apparatus fitted with a short distillation path without thermal decomposition taking place in the process, and that the resulting crude ester contains little or no formic acid, with the result that the ester can be transesterified catalytically with an alcohol in a manner known per se to give cyclooctanol.

In addition, it has been found that because of the instability of formic acid, it is favorable to separate off the majority of unreacted formic acid prior to distillation of the cyclooctyl formate and work it up separately. This is advantageously effected by first separating the phases into two phases (phases A and B) and extracting the cyclooctyl formate from phase A. The extract is added to phase B and passed to the distillative work-up of the cyclooctyl formate. The formic acid is distilled in a separate column and the top product obtained is pure formic acid, which can be reintroduced into the reaction. A water/acid mixture is left over as the bottom product.

DETAILED DESCRIPTION OF THE INVENTION

The invention therefore provides a process for the preparation of cyclooctanol from cyclooctene comprising:

a. reaction of cyclooctene with formic acid in the absence of an added catalyst to produce a two-phase reaction mixture containing cyclooctyl formate and residual formic acid, b. separation of the two phases into a lower phase rich in formic acid (phase A) and an upper phase low in formic acid (phase B), c. extraction of cyclooctyl formate from phase A to obtain an extract, d. combination of phase B and the extract from phase A, e. distillative work-up of the combination of phase B and the extract from phase A in an apparatus fitted with a short distillation path to obtain crude cyclooctyl formate, and f. catalytic transesterification of the cyclooctyl formate of said crude cyclooctyl formate with an alcohol to produce cyclooctanol.

The first stage of the process according to the invention requires neither solvent nor externally added catalyst.

The process according to the invention has the advantage that a column is dispensed with but nevertheless the formic acid, which is usually present in large excess in the reaction, is separated off completely from the ester. Only because of this is it possible to transesterify the ester with small amounts of a catalyst without producing noteworthy amounts of salt as waste material. Catalysts which can be used for the transesterification are, preferably, alkali metal and alkaline earth metal compounds, such as, for example, alkali metal and alkaline earth metal alkoxides. Examples which may be mentioned are sodium methoxide, sodium ethoxide and potassium methoxide.

The molar ratio of cyclooctene to formic acid is from 1:1 to 1:6, preferably from 1:2 to 1:4.

The reaction temperature is between 60 and 100° C., preferably between 70 and 90° C. A reaction temperature of approximately 80° C. is particularly preferred. The process can be carried out discontinuously or continuously.

After the reaction, which is complete in the case of the discontinuous procedure in from 2 to 10 hours, preferably in from 4 to 8 hours, the reaction mixture is cooled. After separation of the phases, the cyclooctane formate of phase A rich in formic acid is extracted using a nonpolar solvent. Suitable solvents are linear or branched aliphatic hydrocarbons having from 5 to 10 carbon atoms, such as, for example, pentane, hexane and octane; cycloaliphatic hydrocarbons such as, for example, cyclohexane; aromatic hydrocarbons, such as, for example, benzene or toluene; and (cyclo)olefinic hydrocarbons such as, for example, cyclooctene. Preference is given to using cyclooctene because it is already a constituent of the reaction system.

Distillative work-up is carried out in an evaporator with a short distillation path, such as, for example, a falling-film evaporator, a short-path evaporator or a thin-film evaporator.

Following extraction, the crude formic acid is worked up in a column having at least 10 theoretical plates, a virtually anhydrous acid distilling off and a higher-boiling formic acid/water mixture being left over in the reboiler, which mixture is disposed of, for example by combustion. The water is formed as a result of slight thermal decomposition of the formic acid during the reaction. It must be removed because it interferes with the reaction with the cyclooctene. The water content of the formic acid used for the reaction should therefore preferably be <1% by weight.

Having generally described this invention, a further understanding can be obtained by reference to certain specific examples which are provided herein for purposes of illustration only and are not intended to be limiting unless otherwise specified.

EXAMPLES

Example 1
Discontinuous Procedure

A 50 l glass stirred reboiler fitted with stirrer, thermometer and heating with an oil thermostat was used. 22 kg (0.2 kmol) of cyclooctene and 28 kg (0.6 kmol) of formic acid were combined in the reboiler and stirred intensively at 80° C. for 6 hours. After cooling to <30° C., the phases, which separated within a few minutes, were divided. The upper B phase weighed 22.7 kg and comprised

| | |
|---|---|
| HCOOH | 7.6% |
| COF | 26.3% |
| COE | 60.4% |
| H$_2$O | 0.1% |
| remainder | 5.6% | and the lower A phase weighed 27.3 kg and comprised

| | |
|---|---|
| HCOOH | 78.7% |
| COF | 16.8% |
| COE | 3.4% |
| H$_2$O | 0.7% |
| remainder | 0.4% |

HCOOH=formic acid, COF=cyclooctyl formate, COE=cyclooctene, H$_2$O=water

The lower phase was extracted with 3×8.5 kg of COE in a 25 l stirred apparatus. The phases were separated and analyzed:

The course of the extraction is given in the table below:

| Phase | Amount (kg) | H$_2$O (%) | HCOOH (%) | COE (%) | COF (%) | Remainder |
|---|---|---|---|---|---|---|
| 1$^{st}$ upper | 12.5 | 0.09 | 4.94 | 73.39 | 18.42 | 3.16 |
| 2$^{nd}$ upper | 10.1 | 0 | 2.40 | 85.45 | 9.32 | 2.83 |
| 3$^{rd}$ upper | 9.4 | 0 | 1.46 | 91.18 | 4.32 | 3.04 |
| 1$^{st}$ lower | 23.3 | 0.83 | 88.63 | 1.73 | 8.67 | 0.14 |
| 2$^{nd}$ lower | 21.7 | 0.92 | 93.50 | 1.24 | 4.20 | 0.14 |
| 3$^{rd}$ lower | 20.8 | 0.97 | 95.56 | 1.04 | 2.06 | 0.37 |

The total amount of COF in all of the upper phases was 61.6 mol. This gives a yield of 30.8%, based on COE used: The selectivity was 99.9%, i.e. no thermal decomposition was observed during the reaction or the first work-up.

Example 2
2.1 Reaction, Continuous Procedure

A 30 l glass stirred reboiler fitted with stirrer, thermometer and two feed receivers was used, and an oil thermostat was used for heating. The reaction was carried out continuously and initially 11.0 kg (100 mol) of cyclooctene and 14.0 kg (304 mol) of formic acid (99.9% strength) were combined in the reboiler, heated to 80° C. and stirred intensively at 80° C. for 6 hours.

For the continuous operation, 2.6 l/h=2.2 kg/h (20 mol/h) of cyclooctene and
2.3 l/h=2.8 kg/h (60 mol/h) of formic acid were pumped into the reboiler. Over a period of 18 hours, a total of 50.4 kg of formic acid and 39.6 kg of cyclooctene were continuously metered in, and at the same rate a reaction mixture was drawn off, which was passed to a settling container for phase separation.

The reaction discharge comprised 43.0 kg of an upper phase and 46.2 kg of a lower phase having the following compositions:

| | COE (%) | COF (%) | HCOOH (%) | Remainder |
|---|---|---|---|---|
| Upper phase | 64.7 | 21.1 | 7.0 | 7.2 |
| Lower phase | 2.2 | 10.9 | 84.9 | 2.0 |

This gives a yield of 26.0%, based on COE used, and of 99.9%, based on COE reacted.

2.2 Distillative Work-up of the Formic Acid

Use was made of a continuous distillation column with at least 10 theoretical plates. Distillation was carried out on 207.5 kg of an extracted formic acid phase having the following composition:

| | |
|---|---|
| HCOOH | 98.5% |
| H$_2$O | 0.9% |
| COF | 0.5% |
| COE | 0.1% |

The distillate obtained was 178.6 kg of formic acid containing 0.003% of water. 22.8 kg of formic acid/water mixture containing 10.6% of water remained in the reboiler. In the distillation, COF decomposes to give COE and HCOOH. The COE is present in the distillate in an amount of about 0.3%. Only slight decomposition of the formic acid occurred.

2.3 Work-up of Crude Cyclooctyl Formate Using a Thin-film Evaporator

The crude cyclooctyl formate present after extraction still comprised 61.0% cyclooctene and small amounts of formic acid, which were distilled off under gentle conditions in a thin-film evaporator made of glass and having a surface area of 0.1 m$^2$. The distillation conditions were:

| | |
|---|---|
| Transition temperature | 80° C. |
| Oil initial fraction temperature | 145° C. |
| Pressure | 100 hPa |
| Feed amount | 3.0 l/h |

Feed, 75.3 kg, having the following components:

| | |
|---|---|
| HCOOH | 7.3% |
| COF | 22.8% |
| COE | 61.0% |
| remainder | 8.9% |

The distillates obtained were: upper phase: 51.7 kg, and lower phase 6.0 kg

Composition:

|  | COF (%) | COE (%) | HCOOH (%) | Remainder |
|---|---|---|---|---|
| Upper phase | 7.7 | 82.5 | 0.7 | 9.1 |
| Lower phase | 3.8 | 0.4 | 90.7 | 5.1 |

The bottom product, 17.5 kg, comprised 78.6% of cyclooctyl formate and 5.5% of cyclooctene, but no formic acid. No decomposition was observed.

2.4 Transesterification of the Cyclooctyl Formate to Cyclooctanol

Since the concentrated cyclooctyl formate did not comprise formic acid, it could be transesterified in a customary manner using methanol and sodium methoxide as catalyst.

Use was made of 9.95 kg of bottom product having the above composition, 6.41 kg of methanol and 3×200 ml of sodium methoxide solution, 30% strength, which was in each case metered in after 2 hours. At reboiler temperatures around 53° C., methyl formate was formed continuously, which was distilled off. After just 6 hours the reaction was complete. Distillative work-up gave 5.28 kg of cyclooctanol having a purity of 99.8%. Yield: 82.2% based on cyclooctyl formate used. The total yield over all fractions was 96.2%.

Obviously, numerous modifications and variations of the present invention are possible in light of the above teachings. It is therefore to be understood that within the scope of the appended claims, the invention may be practiced otherwise than as specifically described herein.

The disclosure of German priority application No. 19944874.4, filed Sep. 18, 1999, is hereby incorporated by reference.

What is claimed is:

1. A process for the preparation of cyclooctanol from cyclooctene comprising:
    a. reaction of cyclooctene with formic acid in the absence of an added catalyst to produce a two-phase reaction mixture containing cyclooctyl formate and residual formic acid,
    b. separation of the two phases into a lower phase rich in formic acid (phase A) and an upper phase low in formic acid (phase B),
    c. extraction of cyclooctyl formate from phase A to obtain an extract,
    d. combination of phase B and the extract from phase A,
    e. distillative work-up of the combination of phase B and the extract from phase A in an apparatus fitted with a short distillation path to obtain crude cyclooctyl formate, and
    f. catalytic transesterification of the cyclooctyl formate of said crude cyclooctyl formate with an alcohol to produce cyclooctanol.

2. The process as claimed in claim 1, wherein the cyclooctene and formic acid are reacted in a molar ratio of from 1:2 to 1:4.

3. The process as claimed in claim 1, wherein the formic acid has a water content of <1% by weight.

4. The process as claimed in claim 2, wherein the formic acid has a water content of <1% by weight.

5. The process as claimed in claim 1, wherein the reaction of cyclooctene and formic acid is carried out at a reaction temperature of between 60° C. and 100° C.

6. The process as claimed in claim 1, wherein water that is formed during the reaction and dissolved in the formic acid is essentially removed from the formic acid by distillation, to form essentially anhydrous formic acid, and wherein said essentially anhydrous formic acid is returned to the reaction.

7. The process as claimed in claim 1, wherein the extraction is carried out using an aliphatic, cycloaliphatic or aromatic hydrocarbon solvent.

8. The process as claimed in claim 7, wherein the solvent is cyclooctene.

9. The process as claimed in claim 1, wherein the apparatus fitted with a short distillation path is a thin-film evaporator.

10. The process as claimed in claim 2, wherein the apparatus fitted with a short distillation path is a thin-film evaporator.

11. The process as claimed in claim 3, wherein the apparatus fitted with a short distillation path is a thin-film evaporator.

12. The process as claimed in claim 4, wherein the apparatus fitted with a short distillation path is a thin-film evaporator.

13. The process as claimed in claim 1, wherein the apparatus fitted with a short distillation path is a falling-film evaporator.

14. The process as claimed in claim 2, wherein the apparatus fitted with a short distillation path is a falling-film evaporator.

15. The process as claimed in claim 3, wherein the apparatus fitted with a short distillation path is a falling-film evaporator.

16. The process as claimed in claim 4, wherein the apparatus fitted with a short distillation path is a falling-film evaporator.

17. The process as claimed in claim 1, wherein the apparatus fitted with a short distillation path is a short-path evaporator.

18. The process as claimed in claim 2, wherein the apparatus fitted with a short distillation path is a short-path evaporator.

19. The process as claimed in claim 3, wherein the apparatus fitted with a short distillation path is a short-path evaporator.

20. The process as claimed in claim 4, wherein the apparatus fitted with a short distillation path is a short-path evaporator.

* * * * *